United States Patent
Detemmerman et al.

(10) Patent No.: US 10,889,738 B2
(45) Date of Patent: Jan. 12, 2021

(54) ROOM TEMPERATURE CURABLE COMPOSITIONS

(71) Applicant: Dow Silicones Corporation, Midland, MI (US)

(72) Inventors: Tommy Detemmerman, Wezembeek-oppem (BE); Tatiana Dimitrova, Braine-l'Alleud (BE); Frederic Gubbels, Houtain-le-Val (BE)

(73) Assignee: Dow Silicones Corporation, Midland, MI (US)

( * ) Notice: Subject to any disclaimer, the term of this patent is extended or adjusted under 35 U.S.C. 154(b) by 187 days.

(21) Appl. No.: 15/777,380

(22) PCT Filed: Nov. 18, 2016

(86) PCT No.: PCT/EP2016/078206
§ 371 (c)(1),
(2) Date: May 18, 2018

(87) PCT Pub. No.: WO2017/085296
PCT Pub. Date: May 26, 2017

(65) Prior Publication Data
US 2020/0063009 A1    Feb. 27, 2020

(30) Foreign Application Priority Data

Nov. 20, 2015 (GB) .................................. 1520461.3
Nov. 2, 2016 (GB) .................................. 1618505.0

(51) Int. Cl.

| | |
|---|---|
| *C08L 83/04* | (2006.01) |
| *C09J 183/04* | (2006.01) |
| *A61K 8/02* | (2006.01) |
| *A61K 8/86* | (2006.01) |
| *A61K 8/89* | (2006.01) |
| *A61L 15/22* | (2006.01) |
| *A61L 31/06* | (2006.01) |
| *A61Q 19/00* | (2006.01) |
| *C09J 5/06* | (2006.01) |

(52) U.S. Cl.
CPC .......... *C09J 183/04* (2013.01); *A61K 8/0208* (2013.01); *A61K 8/86* (2013.01); *A61K 8/89* (2013.01); *A61L 15/225* (2013.01); *A61L 31/06* (2013.01); *A61Q 19/00* (2013.01); *C09J 5/06* (2013.01); *A61K 2800/10* (2013.01); *C09J 2301/416* (2020.08); *C09J 2471/00* (2013.01); *C09J 2483/00* (2013.01)

(58) Field of Classification Search
CPC .............................. C08L 83/04; C09J 183/04
See application file for complete search history.

(56) References Cited

U.S. PATENT DOCUMENTS

| | | | |
|---|---|---|---|
| 4,247,442 A * | 1/1981 | Shimizu .................. | C08K 5/47 524/83 |
| 4,831,070 A | 5/1989 | McInally et al. | |
| 4,968,760 A | 11/1990 | Schiller et al. | |
| 5,138,009 A | 8/1992 | Inoue | |
| 5,223,495 A * | 6/1993 | Inoue .................. | C09D 143/04 524/188 |
| 6,545,104 B1 | 4/2003 | Mueller et al. | |
| 2003/0065086 A1 | 4/2003 | Kosal | |
| 2005/0048124 A1* | 3/2005 | Sarangapani .......... | A61K 33/38 424/486 |
| 2005/0288415 A1 | 12/2005 | Beers et al. | |
| 2007/0173596 A1 | 7/2007 | Landon et al. | |
| 2007/0212314 A1 | 9/2007 | Murphy et al. | |
| 2008/0295960 A1 | 12/2008 | Schalau, II et al. | |
| 2008/0311396 A1 | 12/2008 | Hamada et al. | |
| 2010/0069531 A1* | 3/2010 | Sakamoto ............... | C08L 83/04 523/177 |
| 2010/0234517 A1 | 9/2010 | Plantenberg et al. | |
| 2012/0109036 A1 | 5/2012 | Sambasivam et al. | |
| 2013/0338289 A1 | 12/2013 | Jadot et al. | |
| 2014/0220843 A1 | 8/2014 | Liu et al. | |
| 2014/0350176 A1 | 11/2014 | Fisher et al. | |

FOREIGN PATENT DOCUMENTS

| | | |
|---|---|---|
| CN | 1914281 A | 2/2007 |
| CN | 104559910 A | 4/2015 |
| CN | 104710960 A | 6/2015 |
| CN | 104774587 A | 7/2015 |
| EP | 0315333 A2 | 5/1989 |
| EP | 0802233 A2 | 10/1997 |
| GB | 2518468 A | 3/2015 |
| JP | 56-076452 * | 6/1981 |
| JP | S5676453 A | 6/1981 |
| JP | 2002536526 A | 10/2002 |
| JP | 2008069869 A | 3/2008 |
| JP | 2014513158 A | 5/2014 |
| WO | 2005021058 A2 | 3/2005 |
| WO | 2008039654 A2 | 4/2008 |
| WO | WO2011051236 A2 | 5/2011 |
| WO | WO2012119940 A1 | 9/2012 |
| WO | WO2015082877 A1 | 6/2015 |
| WO | 2015121626 A1 | 8/2015 |

OTHER PUBLICATIONS

English language translation (machine generated) JP 56-076452, Jun. 1981.*
English language abstract JP 56-07652, Jun. 1981.*
Machine assisted English translation of CN104559910A obtained from https://patents.google.com/patent on Apr. 7, 2020, 4 pages.
(Continued)

*Primary Examiner* — Margaret G Moore
(74) *Attorney, Agent, or Firm* — Warner Norcross + Judd LLP

(57) ABSTRACT

A room temperature curable sealant/adhesive composition is disclosed. The room temperature curable sealant/adhesive composition comprises: (A) one or more organopolysiloxanes; (B) a hydrophilic material; (C) a cross-linker; (D) a titanate or zirconate catalyst; and (E) one or more optional ingredients. A silicone elastomer formed therefrom and related methods are also disclosed.

20 Claims, No Drawings

(56) References Cited

OTHER PUBLICATIONS

Machine assisted English translation of CN104710960A obtained from https://patents.google.com/patent on Apr. 7, 2020, 4 pages.
Machine assisted English translation of CN104774587A obtained from https://patents.google.com/patent on Apr. 7, 2020, 6 pages.
Machine assisted English translation of JP2008069869A obtained from https://patents.google.com/patent on Apr. 3, 2020, 8 pages.
PCT/EP2016/078206 International Search Report dated Jan. 26, 2017, 4 pages.
Chen, Wei-Fu et al., "Covalently Cross-Linked Perfluorosulfonated Membranes with Polysiloxane Framework", Macromolecules 2007, vol. 40, No. 6, pp. 1987-1994.
Zhongzhan, Sun et al., "Synthesis and characterization of a new-type Schiff base side-chain polysiloxan[e] liquid crystal containing sulfonate groups", New Chemical Materials 2011, vol. 39, No. 5, pp. 56-58.
Machine assisted English translation of CN1914281A obtained from https://patents.google.com/patent on Jul. 22, 2020, 42 pages.
Machine assisted English translation of JPS5676453A obtained from https://worldwide.espacenet.com/ on Jul. 23, 2020, 5 pages.

\* cited by examiner

ROOM TEMPERATURE CURABLE COMPOSITIONS

CROSS-REFERENCE TO RELATED APPLICATIONS

This application is the National Stage of International Application No. PCT/EP2016/078206 filed on 18 Nov. 2016, which claims priority to and all advantages of GB Patent Application No. 1618505.0 filed on 2 Nov. 2016 and GB Patent Application No. 1520461.3 filed on 20 Nov. 2015, the contents of which are hereby incorporated by reference.

This relates to silicone room temperature curable sealant/adhesive compositions, in particular such compositions which (upon several hours of contact with water) do not repel water, but rather retain and pick-up water and/or can be wetted by aqueous materials subsequent to exposure.

Typically cured silicone materials are substantially hydrophobic and have low surface energy surfaces. Some of their most important uses, e.g. as sealants and/or caulks utilise these physical properties as they e.g. require minimal if any water ingress.

However one drawback to having low surface energies is that they are wetted by very few materials (if at all); thus making the silicone sealants extremely difficult to paint. Silicone room temperature curable sealant/adhesive compositions may generate vapour permeable elastomeric materials which can be formulated to be both inert to the skin and provide adhesion to skin, e.g. in the form of pressure sensitive adhesives. Such materials have a wide range of applications including (without being restricted to) medical adhesives, wound care coatings/pads, skin care and ostomy care.

EP0315333 describes mouldable elastomeric pressure sensitive adhesive compositions and their preparation, particularly solventless, mouldable compositions which can be moulded and cured at room temperature and which are useful for making medical adhesives. WO2015/082877 describes skin compatible curing adhesives for adhering devices or appliances to the mammalian body.

Hence, there are reasons for seeking silicone room temperature curable sealant/adhesive compositions and resulting cured elastomers which do not repel water, but rather retain and pick-up water and/or can be wetted by aqueous materials subsequent to exposure.

There is provided herein a silicone room temperature curable sealant/adhesive composition comprising, A) 50-95% by weight of one or more organopolysiloxanes selected from
  (i) $(R''O)_{3-a}(R)_a Si-Z-(Si(R)_2-O)_x-Si(R)_2-Z-Si(OR'')_{3-a}(R)_a$ where each R is free of aliphatic unsaturation and is selected from the group consisting of monovalent hydrocarbon, monovalent halohydrocarbon, and monovalent cyanoalkyl radicals of 1 to 18 inclusive carbon atoms, each R" is a monovalent hydrocarbon group having 1 to 6 carbon atoms Z is a divalent hydrocarbon radical or combination of divalent hydrocarbon radicals and siloxane radicals, a is 0 or 1, and x is of a value such that the polymer has a viscosity of from 0.5 to 3000 Pa·s at 25° C.;
  (ii) alpha, omega-diorganopolysiloxane of the formula

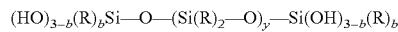

where each R is free of aliphatic unsaturation and is selected from the group consisting of monovalent hydrocarbon, monovalent halohydrocarbon, and monovalent cyanoalkyl radicals of 1 to 18 inclusive carbon atoms, b is 0, 1 or 2, and y is of a value such that the polymer has a viscosity of from 0.5 to 3000 Pa·s at 25° C. and a number average molecular weight ($M_n$) of from 1000 to 1000000; or
  (iii) mixtures of the above B) 5-35% by weight of hydrophilic, material selected from
  (i) Hydrophilic and/or water soluble resins based on polyethylene oxide and/or polypropylene oxide
  (ii) One or more anionic surfactants
  (iii) Polymers containing ionisable groups, such as sulphonate groups, acetate groups, sulphate groups;
  (iv) mixtures of two or more of (i), (ii) and (iii)

C) 0.5-7.5% by weight of cross-linker selected from a silane or siloxane cross linker containing at least 2 but typically 3 or more alkoxy or alkenyloxy groups, or silyl functional molecules having at least 2 silyl groups, each silyl group containing at least one alkoxy or alkenyloxy group.

D) 0.5-5% by weight titanate or zirconate catalyst;

E) One or more optional ingredients selected from fillers, co-catalysts; rheological modifiers; plasticisers, adhesion promoters, compatibilizer', pigments, heat stabilizers, flame retardants, UV stabilizers, chain extenders, electrically and/or heat conductive fillers, and/or fungicides/biocides; wherein the total % weight of A+B+C+D+E is 100%.

Component A) is 50-95% by weight of one or more organopolysiloxanes selected from A) i, A) ii or A) iii as described above.

A) i is an organopolysiloxane of the structure: $(R''O)_{3-a}(R)_a Si-Z-(Si(R)_2-O)_x-Si(R)_2-Z-Si(OR'')_{3-a}(R)_a$ in which each R is free of aliphatic unsaturation and is selected from the group consisting of monovalent hydrocarbon, monovalent halohydrocarbon, and monovalent cyanoalkyl radicals of in each case 1 to 18 inclusive carbon atoms alternatively in each case 1 to 10 carbon atoms, further alternatively in each case 1 to 6 carbon atoms such as methyl, ethyl, propyl, or butyl, each R" is a monovalent hydrocarbon group having 1 to 6 carbon atoms alternatively is methyl, ethyl, propyl, or butyl, Z is a divalent hydrocarbon radical, alternatively a divalent hydrocarbon radical having from 1 to 10 carbon atoms, or further alternatively 1 to 6 carbon atoms or a combination of said divalent hydrocarbon radicals and divalent siloxane radicals, a is 0 or 1, and x is of a value such that the polymer has a viscosity of from 0.5 to 3000 Pa·s at 25° C.; (Viscosity measurement were measured using a suitable Brookfield viscometer).

A) ii is an alpha, omega-diorganopolysiloxane of the formula

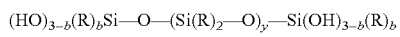

where each R is free of aliphatic unsaturation and is selected from the group consisting of monovalent hydrocarbon, monovalent halohydrocarbon, and monovalent cyanoalkyl radicals of in each case 1 to 18 inclusive carbon atoms, alternatively in each case 1 to 10 carbon atoms, further alternatively in each case 1 to 6 carbon atoms such as methyl, ethyl, propyl, or butyl, b is 0, 1 or 2, and y is of a value such that the polymer has a viscosity of from 0.5 to 3000 Pa·s at 25° C. and a number average molecular weight ($M_n$) of from 1000 to 1000000; or A) iii are mixtures of A) i and A) ii. The mixture may be in a ratio of A) i to A) ii of from 10:1 to 1:10.

Component B in the composition comprises from 5-35% by weight of the composition of a hydrophilic material. The hydrophilic, material may be B) (i) which are hydrophilic and/or water soluble polyoxyalkylene resins and/or polymers. Such polyoxyalkylene compounds preferably comprise predominantly oxyalkylene polymer comprised of recurring oxyalkylene units, (—$C_nH_{2n}$—O—) illustrated by the average formula (—$C_nH_{2n}$—O—)$_y$, wherein n is an integer from 2 to 4 inclusive and y is an integer of at least four. Moreover, the oxyalkylene units are not necessarily identical throughout the polyoxyalkylene monomer, but can differ from unit to unit. A polyoxyalkylene for example, can be comprised of oxyethylene units (—$C_2H_4$—O—), oxypropylene units (—$C_3H_6$—O—) or oxybutylene units (—$C_4H_8$—O—); or mixtures thereof. The number average molecular weight of each polyoxyalkylene polymer may range from about 300 to tens of millions. Herein high number average molecular weight polymers/resins e.g. >50 000, alternatively >75 000, alternatively, 75 000 to 20 000 000, alternatively 75 000 to 10 000 000 may be used. The number average molecular weight is the total weight of the sample divided by the number of molecules in the sample and was determined by gel permeation chromatography (GPC) using a triple detection capability (Viscotek TDA305 unit) composed of a differential refractometer, an online differential pressure viscometer and low angle light scattering (LALS: 7° and 90° angles of detection).

The hydrophilic material may be B) (ii) anionic surfactants such as sodium/potassium sulphonates; alkenyl sulphonates; alkyl sulphates, alkyl-benzene sulphonates; potassium alkyl phosphates, alkyl succinates; alkyl sulphosuccinates and N-alkyl sarcosinates and sodium, magnesium, ammonium, and the mono-, di- and triethanolamine salts of alkyl and aralkyl sulphates as well as the salts of alkaryl sulphonates. The alkyl groups generally have a total of from about 12 to 21 carbon atoms, may be unsaturated, and are preferably fatty alkyl groups. The sulphates may be sulphate ethers containing one to ten ethylene oxide or propylene oxide units per molecule. Preferably, the sulphate ethers contain 2 to 3 ethylene oxide units.

Typical anionic surfactants include, among others, sodium lauryl sulphate, sodium lauryl ether sulphate, ammonium lauryl sulphate, triethanolamine lauryl sulphate, sodium C14-16 olefin sulphonate, ammonium pareth-25 sulphate (ammonium salt of a sulphated polyethylene glycol ether of a mixture of synthetic C12-15 fatty alcohols), sodium myristyl ether sulphate, ammonium lauryl ether sulphate, disodium monooleamidosulphosuccinate, ammonium lauryl sulphosuccinate, sodium dodecylbenzene sulphonate, triethanolamine dodecylbenzene sulphonate and sodium N-lauroyl sarcosinate. The lauryl sulphates include monoethanolamine, triethanolamine, ammonium and sodium lauryl sulphates.

Other anionic surfactants include alkali metal sulphoricinates, sulphonated glyceryl esters of fatty acids such as sulphonated monoglycerides of coconut oil acids, salts of sulphonated monovalent alcohol esters such as sodium oleylisethianate, amides of amino sulphonic acids such as the sodium salt of oleyl methyl tauride, sulphonated products of fatty acids nitriles such as palmitonitrile sulphonate, sulphonated aromatic hydrocarbons such as sodium alpha-naphthalene monosulphonate, condensation products of naphthalene sulphonic acids with formaldehyde, sodium octahydroanthracene sulphonate, alkylbenzenesulphonic acid alkali metal salts exemplified by hexylbenzenesulphonic acid sodium salt, octylbenzenesulphonic acid sodium salt, decylbenzenesulphonic acid sodium salt, dodecylbenzenesulphonic acid sodium salt, cetylbenzenesulphonic acid sodium salt, and myristylbenzenesulphonic acid sodium salt, sulphuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulphonic acid.

The hydrophilic material may be B) (iii) which are polymers containing ionizable groups, e.g. pendent sulphonate groups, acetate groups, sulphate groups. Examples include but are not limited to homopolymers and copolymers comprising vinylsulphonic, styrenesulphonic, naphthalenesulphonic or acrylamidoalkylsulphonic units and their salts. Polyvinylsulphonic acid salts may include those having a molecular weight of approximately between 1000 and 100 000, and also the copolymers with an unsaturated comonomer such as acrylic or methacrylic acids and their esters, and also acrylamide or its derivatives, vinyl ethers and vinylpyrrolidone. Sodium salts of polystyrenesulphonic acid, polyacrylamidosulphonic acid salts, e.g. for the sake of example polyacrylamidoethylpropanesulphonic acid. Polyvinyl alcohols may be utilized and are typically prepared by saponification of polyvinyl acetate. Component B in the composition may also comprise any suitable mixture of B) (i) and/or B) (ii) and B) (iii) in any suitable amount.

Component C is a suitable cross linker containing at least 2 but typically 3 or more alkoxy or alkenyloxy groups. Any suitable alkoxy type or alkenoxy type cross-linker may be used. These include one or more silanes or siloxanes which contain silicon bonded alkoxy groups such as methoxy, ethoxy or propoxy groups and silicon bonded alkenyloxy groups (for example isopropenyloxy and 1-ethyl-2-methylvinyloxy). Another type of cross-linker that might be used are silyl functional molecules having at least 2 silyl groups, each silyl group containing at least one hydrolysable group.

In the case of siloxane based cross-linkers and silyl functional molecules the molecular structure can be straight chained, branched, or cyclic.

The crosslinkers (C) may have two but preferably has three or four silicon-bonded alkoxy and/or alkenyloxy groups per molecule which are reactive with the condensable groups in organopolysiloxane polymer (A). When the crosslinker is a silane and when the silane has three silicon-bonded alkoxy and/or alkenyloxy groups per molecule, the fourth group is suitably a non-hydrolysable silicon-bonded organic group. These silicon-bonded organic groups are suitably hydrocarbyl groups which are optionally substituted by halogen such as fluorine and chlorine. Examples of such fourth groups include alkyl groups (for example methyl, ethyl, propyl, and butyl); cycloalkyl groups (for example cyclopentyl and cyclohexyl); alkenyl groups (for example vinyl and allyl); aryl groups (for example phenyl, and tolyl); aralkyl groups (for example 2-phenylethyl) and groups obtained by replacing all or part of the hydrogen in the preceding organic groups with halogen. Preferably however, the fourth silicon-bonded organic groups is methyl.

Silanes which can be used as crosslinkers include alkyltrialkoxysilanes such as methyltrimethoxysilane (MTM) and methyltriethoxysilane, alkenyltrialkoxy silanes such as vinyltrimethoxysilane and vinyltriethoxysilane, isobutyltrimethoxysilane (iBTM). Other suitable silanes include ethyltrimethoxysilane, vinyltriethoxysilane, phenyltrimethoxysilane, 3,3,3-trifluoropropyltrimethoxysilane, phenyltripropionoxysilane, methyltris(isopropenoxy)silane, vinyltris(isopropenoxy)silane, ethylpolysilicate, n-propylorthosilicate, ethylorthosilicate, or any combination of two or more of the above.

A typical silane may be described by $R''_{4-r}Si(OR^5)_r$ wherein $R^5$ is an alkyl group having from 1 to 6 carbon atoms and r has a value of 2, 3 or 4. R" is an organic radical selected from linear and branched alkyls, allyls, phenyl and substituted phenyls. Typical silanes are those wherein R" represents methyl, ethyl or vinyl or isobutyl. In some instances, $R^5$ represents methyl or ethyl and r is 3.

Another type of suitable crosslinkers (ii) are molecules of the type $Si(OR^5)_4$ where $R^5$ is an alkyl group having from 1 to 6 carbon atoms, alternatively propyl, ethyl or methyl. Partials condensates of $Si(OR^5)_4$ may also be considered.

Alternatively Crosslinkers (C) may comprise the here before described silyl functional molecules having at least 2 silyl groups, each silyl group containing at least one hydrolysable group.

For the sake of the disclosure herein silyl functional molecule is a silyl functional molecule containing two or more silyl groups, each silyl group containing at least one hydrolysable group. Hence, a disilyl functional molecule comprises two silicon atoms each having at least one hydrolysable group, where the silicon atoms are separated by an organic or siloxane spacer. Typically, the silyl groups on the disilyl functional molecule may be terminal groups. The spacer may be a polymeric chain. The crosslinker C) may be a disilyl functional polymer, that is, a polymer containing two silyl groups, each containing at least one hydrolysable group such as described by $R''_{3-y} Si(OR^5)_y$—Rv-$Si(OR^5)_z R''_{3-z}$ where R" and $R^5$ are as described above, y and z are independently an integer of 1, 2 or 3, alternatively 2 or 3. Rv is a divalent hydrocarbon radical, alternatively a divalent hydrocarbon radical having from 1 to 10 carbon atoms, or further alternatively 1 to 6 carbon atoms or a combination of said divalent hydrocarbon radicals and divalent siloxane radicals.

The silyl (e.g. disilyl) functional crosslinker may have a siloxane or organic polymeric backbone. In the case of such siloxane or organic based cross-linkers the molecular structure can be straight chained, branched, cyclic or macromolecular. In the case of siloxane based polymers the viscosity of the cross-linker will be within the range of from 0.5 mPa·s to 80,000 mPa·s at 25° C.

Examples of disilyl polymeric crosslinkers (ii) with a silicone or organic polymer chain bearing alkoxy functional end groups include polydimethylsiloxanes having at least one trialkoxy terminal where the alkoxy group may be a methoxy or ethoxy group. Examples might include or 1,6-bis(trimethoxy silyl)hexane hexamethoxydisiloxane, hexaethoxydisiloxane, hexa-n-propoxydisiloxane, hexa-n-butoxydisiloxane, octaethoxytrisiloxane, octa-n-butoxytrisiloxane and decaethoxy tetrasiloxane.

The composition herein additionally includes component D 0.5-5% by weight of a titanate or zirconate catalyst. Titanate and/or zirconate based catalysts may comprise a compound according to the general formula $Ti[OR^{22}]_4$ where each $R^{22}$ may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of $R^{22}$ include but are not restricted to methyl, ethyl, propyl, isopropyl, butyl, tertiary butyl and a branched secondary alkyl group such as 2,4-dimethyl-3-pentyl. Preferably, when each $R^{22}$ is the same, $R^{22}$ is an isopropyl, branched secondary alkyl group or a tertiary alkyl group, in particular, tertiary butyl. Alternatively, the titanate may be chelated. The chelation may be with any suitable chelating agent such as an alkyl acetylacetonate such as methyl or ethylacetylacetonate.

Dependent on the end use for which the composition is to be used, compositions as described above may contain, as optional ingredients E), which are conventional to the formulation of silicone rubber sealants and the like. For example, the compositions may contain one or more finely divided, reinforcing fillers such as high surface area fumed and precipitated silicas including rice hull ash, commercial examples include for the sake of example AEROSIL® R 974 and AEROSIL® R 812. from Evonik, and to a degree calcium carbonate, or additional non-reinforcing fillers such as crushed quartz, diatomaceous earths, barium sulphate, iron oxide, zeolites e.g. Zeolite 4A, titanium dioxide and carbon black, talc, wollastonite. Other fillers which might be used alone or in addition to the above include aluminite, calcium sulphate (anhydrite), gypsum, calcium sulphate, magnesium carbonate, clays such as kaolin, aluminium trihydroxide, magnesium hydroxide (brucite), graphite, copper carbonate, e.g. malachite, nickel carbonate, e.g. zarachite, barium carbonate, e.g. witherite and/or strontium carbonate e.g. strontianite Aluminium oxide, silicates from the group consisting of olivine group; garnet group; aluminosilicates; ring silicates; chain silicates; and sheet silicates. The olivine group comprises silicate minerals, such as but not limited to, forsterite and $Mg_2SiO_4$. The garnet group comprises ground silicate minerals, such as but not limited to, pyrope; $Mg_3Al_2Si_3O_{12}$; grossular; and $Ca_2Al_2Si_3O_{12}$. Aluninosilicates comprise ground silicate minerals, such as but not limited to, sillimanite; $Al_2SiO_5$; mullite; $3Al_2O_3.2SiO_2$; kyanite; and $Al_2SiO_5$ The ring silicates group comprises silicate minerals, such as but not limited to, cordierite and $Al_3(Mg,Fe)_2[Si_4AlO_{18}]$. The chain silicates group comprises ground silicate minerals, such as but not limited to, wollastonite and $Ca[SiO_3]$.

The sheet silicates group comprises silicate minerals, such as but not limited to, mica; $K_2Al_{14}[Si_6Al_2O_{20}](OH)_4$; pyrophyllite; $Al_4[Si_8O_{20}](OH)_4$; talc; $Mg_6[Si_8O_{20}](OH)_4$; serpentine for example, asbestos; Kaolinite; $Al_4[Si_4O_{10}](OH)_8$; and vermiculite.

The fillers may be surface treated for example with a fatty acid or a fatty acid ester such as a stearate, or with organosilanes, organosiloxanes, or organosilazanes hexaalkyl disilazane or short chain siloxane diols to render the filler(s) hydrophobic and therefore easier to handle and obtain a homogeneous mixture with the other sealant components The surface treatment of the fillers makes the ground silicate minerals easily wetted by the silicone polymer. These surface modified fillers do not clump, and can be homogeneously incorporated into the silicone polymer. This results in improved room temperature mechanical properties of the uncured compositions. Furthermore, the surface treated fillers give a lower conductivity than untreated or raw material.

Other ingredients which may be included in the compositions include but are not restricted to co-catalysts for accelerating the cure of the composition such as metal salts of carboxylic acids and amines; rheological modifiers; plasticisers, adhesion promoters, pigments, Heat stabilizers, Flame retardants, UV stabilizers, Chain extenders, electrically and/or heat conductive fillers, Fungicides and/or biocides and the like (which may suitably by present in an amount of from 0 to 0.3% by weight), water scavengers, (typically the same compounds as those used as cross-linkers or silazanes). It will be appreciated that some of the additives are included in more than one list of additives. Such additives would then have the ability to function in all the different ways referred to.

Typically, for silicone based composition plasticisers are organopolysiloxanes which are unreactive with the siloxane polymer of the composition, such as polydimethylsiloxane having terminal triorganosiloxy groups wherein the organic substituents are, for example, methyl, vinyl or phenyl or combinations of these groups. Such polydimethylsiloxanes normally have a viscosity of from about 5 to about 100,000 mPa·s at 25° C. An example are siloxanes such as $(CH_3)_3Si-O-(Si(R)_2-O)-Si(CH_3)_3$ (commercially available from Dow Corning as Dow Corning® 200 fluid) with viscosity from 100 to 100000 mPa·s at 25° C.

The rheological modifiers include silicone organic co-polymers such as those described in EP 0802233 based on polyols of polyethers or polyesters; non-ionic surfactants selected from the group consisting of polyethylene glycol, polypropylene glycol, ethoxylated castor oil, oleic acid ethoxylate, alkylphenol ethoxylates, copolymers or ethylene oxide (EO) and propylene oxide (PO), and silicone polyether copolymers; as well as silicone glycols.

Any suitable adhesion promoter(s) may be incorporated in a sealant composition in accordance with the present invention. These may include for example alkoxy silanes such as aminoalkylalkoxy silanes, epoxyalkylalkoxy silanes, for example, 3-glycidoxypropyltrimethoxysilane and, mercapto-alkylalkoxy silanes and γ-aminopropyl triethoxysilane, reaction products of ethylenediamine with silylacrylates. Isocyanurates containing silicon groups such as 1,3, 5-tris(trialkoxysilylalkyl) isocyanurates may additionally be used. Further suitable adhesion promoters are reaction products of epoxyalkylalkoxy silanes such as 3-glycidoxypropyltrimethoxysilane with amino-substituted alkoxysilanes such as 3-aminopropyltrimethoxysilane and optionally alkylalkoxy silanes such as methyl-trimethoxysilane. epoxyalkylalkoxy silane, mercaptoalkylalkoxy silane, and derivatives thereof.

Compatibilizers are typically small molecules and or oligomers with preferentially amphiphilic character which can be used to improve the incorporation of the water pick-up component (B) into the silicone polymer (A). These could be nonionic emulsifiers of general structure CxEy, where Cx stands for a saturated, linear or branched, aliphatic chain of x carbon atoms and Ey stands for an oligomeric block of Y oxyalkylene units illustrated by the average formula $(-C_nH_{2n}-O-)_Y$ wherein n is an integer from 2 to 4 inclusive and Y is an integer between 4 and 30. Typically X is between 8 and 30.

Alternative compatibilizers include silicone polyethers. Both poly(ethylene oxide) and mixed poly(ethylene oxide)/poly(propylene oxide) polar blocks may be grafted to the silicone backbone. Both linear block (A-B (AB)n and, A-B-A type) and comb structures are available. Typically A is polyoxyalkylene of Z oxyalkylene units illustrated by the average formula $(-C_nH_{2n}-O-)_z$ wherein n is an integer from 2 to 4 inclusive and Y is an integer between 4 and 50. A polyoxyalkylene for example, can be comprised of oxyethylene units ($-C_2H_4-O-$), oxypropylene units ($-C_3H_6-O-$) or oxybutylene units ($-C_4H_8-O-$); or mixtures thereof. The average molecular weight of each A-fragment may range from about 1000 to 30000.

Typical Fragment B is $(Si(R)_2-O)_x$ in which each R is free of aliphatic unsaturation and is selected from the group consisting of monovalent hydrocarbon, monovalent halohydrocarbon, and monovalent cyanoalkyl radicals of in each case 1 to 18 inclusive carbon atoms alternatively in each case 1 to 10 carbon atoms, further alternatively in each case 1 to 6 carbon atoms such as methyl, ethyl, propyl, or butyl.

Heat stabilizers may include Iron oxides and carbon blacks, Iron carboxylate salts, cerium hydrate, titania, barium zirconate, cerium and zirconium octoates, and porphyrins. Flame retardants may include for example, carbon black, hydrated aluminium hydroxide, and silicates such as wollastonite, platinum and platinum compounds.

Chain extenders may include difunctional silanes which extend the length of the polysiloxane polymer chains before crosslinking occurs and, thereby, reduce the modulus of elongation of the cured elastomer. Chain extenders and crosslinkers compete in their reactions with the functional polymer ends; in order to achieve noticeable chain extension, the difunctional silane must have substantially higher reactivity than the typical trifunctional cross-linker. Suitable chain extenders for condensation cure systems are, for example, Diacetamideosilanes such as dialkyldiacetamidosilanes or alkenylalkyldiacetamidosilanes, particularly methylvinyldi-di(N-methylacetamido)silane diacetoxysilanes, such as dialkyldiacetoxysilanes and alkylalkenyldiacetoxysilanes diaminosilanes, such as dialkyldiaminosilanes or alkylalkenyldiaminosilanes particularly those where each amino group has one Si—N bond and two N—C bonds; dialkoxysilanes such as dialkoxysiloxanes (having from 2 to 25 Si—O linkages), diamidosilanes such as dialkyldiamidosilanes or alkylalkenyldiamidosilanes hexaorganodisilazanes (wherein the organo groups are each independently alkyl groups having 1 to 6 carbon atoms or alkenyl groups having 1 to 6 carbon atoms) diketoximinosilanes such as dialkyldiketoximinosilanes and alkylalkenyldiketoximinosilanes α-aminoalkyldialkoxyalkylsilanes wherein the alkyl and alkoxy groups contain from 1 to 5 carbon atoms, such as α-aminomethyldialkoxymethylsilanes particularly preferred are those where the aminomethyl group is an N,N-dialkylaminomethyl group.

Electrically conductive fillers may include carbon black, metal particles such as silver particles any suitable, electrically conductive metal oxide fillers such as titanium oxide powder whose surface has been treated with tin and/or antimony, potassium titanate powder whose surface has been treated with tin and/or antimony, tin oxide whose surface has been treated with antimony, and zinc oxide whose surface has been treated with aluminium.

Thermally conductive fillers may include metal particles such as powders, flakes and colloidal silver, copper, nickel, platinum, gold aluminium and titanium, metal oxides, particularly aluminium oxide ($Al_2O_3$) and beryllium oxide (BeO); magnesium oxide, zinc oxide, zirconium oxide; Ceramic fillers such as tungsten monocarbide, silicon carbide and aluminium nitride, boron nitride and diamond.

Compositions as hereinbefore described have a reasonably quick room temperature cure time (Skin over time SOT) of between 10-70 minutes, alternatively about 20-30 min. They cure upon exposure to (atmospheric) moisture.

The compositions may be designed to contain only ingredients with no or acceptably low toxicity, i.e. containing no ingredients causing known adverse effects such as skin irritation and/or sensitization or the like. As will be shown in the following examples, when cured elastomers made from the compositions hereinbefore described are able to up water when in contact with water, aqueous solutions or aqueous dispersions. Equally elastomers made from the compositions herein may be formulated to provide for desired strength/hardness and elongation and/or other physical properties and the compositions are storage stable in that they can be stored for a prolonged period of time, without losing more that 50% of their mechanical strength upon cure.

Once cured standard silicone materials are substantially hydrophobic (see for example the comparative example described below) and as such undergoes practically no water ingress. However, elastomers made from the compositions described herein uptake water in an amount of at least 0.01 gram of water per gram of cured sealant, when the cured sealant is immersed in water or phosphate buffer saline for 24 h. Such compositions may therefore be useful as paintable sealants, (expandable) joint fillers and water adsorption sealants. These might find use in the applications where joint expansion is desired; for controlling and/or restraining the aqueous leaks which are not under pressure, as for example in rims of wound care and cosmetic patches, medical devices, diapers, etc.

Alternatively, cured silicones made from the compositions as hereinbefore described are vapour permeable and inert to the skin and can be formulated to provide adhesion to skin, thus making them candidates as adhesives for cosmetic patches, drug-release patches (for both humans and animals), wound dressings (for both humans and animals) and so on. It might be desirable that these compositions absorb the sweat or other body fluids.

EXAMPLES

Definitions

SOT=skin over time

Skin Over Time (SOT) is the time required for a sealant/adhesive composition to cure to the point where it no longer adheres to a clean fingertip lightly touched on the surface thereof. Cure usually takes place at room temperature e.g. 22-25° C. and 25-35% relative humidity (RH).

Cure in Depth (CID): The CID test consists of making a 1 cm thick specimen in a cup, allowing the moisture to penetrate only from the air/sealant interface. Samples are allowed to cure for predefined periods of time e.g. 1, 3 and/or 7 days, subsequent to which the thickness of the resulting cured layer is measured.

WU=water uptake/absorbance

Water absorbance have been tested using well-cured pre-weighed specimens. These were soaked in phosphate buffered saline (PBS). At pre-determined regular intervals the specimens were taken out of the PBS wiped to a dry state and weighed. Alternatively, water can be used instead of PBS.

Formulation (all references to parts are intended to mean parts by weight)

Three masterbatches were made for use in the Examples:
Master batch type 1 was been prepared using 1.75 parts of 1,6-bis(trimethoxy silyl)hexane and 87 parts of trimethoxy silyl terminated siloxane polymer with viscosity of about 63000 mPa·s at 25° C.;
Masterbatch type 2 was prepared using 4 parts of cross linker and 87 parts of the same trimethoxy silyl terminated siloxane polymer;
Masterbatch type 3 was prepared using 8 parts of cross-linker and 87 parts of the same trimethoxy silyl terminated siloxane polymer.

The catalyst in all cases was tetra-n-butyl titanate.

Sealants containing one of the above mentioned masterbatches; different amounts of water pick-up material and catalyst were formulated using a SpeedMixer®DAC 150.1 FV-K. A 1-2 mm thick smear was immediately applied onto a glass surface to determine SOT.

The rest of the sealant samples were then kept in open cylindrical containers (diameter approx. 4 cm, depth of the sample—3 to 4 cm) for 7 days, exposed at the ambient atmosphere (approx. 50% RH) at 21-25° C. After that time, the skin formed on the top of the sealant is removed.

If a cured layer (skin) of 0.5 to 1.5 cm depth has been formed, the composition is deemed to be a suitable one-component sealant (1K). The skin removed from the container is stored for another 24 h to 48 h on a lab bench to allow for complete cure (the side originally facing the bulk was exposed to the atmosphere). Thus obtained cured specimens were then used for evaluation of the water pick up ability of the formulations.

The initial weight of each sample tested was between 2 and 6 grams, depending on the thickness.

If bulk cure is observed (e.g. the entire sample has cured) the material is considered as suitable for a bi-component sealant (2K)

COMPARATIVE EXAMPLE

The following comparative example is a standard formulation comprising masterbatch 1 and catalyst (i.e. no component B).

| | Masterbatch type | Masterbatch g | Catalyst g | SOT min | Type of cure |
|---|---|---|---|---|---|
| Comparative 1 | 1 | 35.64 | 0.36 | 20 | 1K |

| | | | | |
|---|---|---|---|---|
| Time when weight difference Measured (h) | 0 | 22 | 72 | 96 |
| Comparative 1 - weight difference (g) (Initial weight 4.197 g) | 0 | 0.008 | 0.007 | 0.01 |

It will be seen that in the absence of component B of the composition the water take up even after 96 hours was negligible.

Example 1 Compositions Using Component B (i) Water Soluble Resin

Example 1a Composition

In this Example component B in the formulation was of the type B) (i) a Hydrophilic and/or water soluble resin based on polyethylene oxide and/or polypropylene oxide. The resin used was a Polyox® resin type WSR 205 which is commercially available from The Dow Chemical Company. Table 1 shows the composition of the sealants together with the type of cure and SOT.

TABLE 1

| Sample Number | Masterbatch type | Masterbatch, amount (g) | Catalyst amount (g) | Polyox WSR 205 amount (g) | SOT, (min) | Type of cure |
|---|---|---|---|---|---|---|
| 1p | 1 | 35.64 | 0.36 | 4 | 50 | 1k |
| 2p | 1 | 35.28 | 0.72 | 4 | 30 | 1k |
| 3p | 1 | 34.92 | 1.08 | 4 | 35 | 1k |
| 4p | 1 | 34.56 | 1.44 | 4 | 30 | 1k |
| 5p | 1 | 34.2 | 1.8 | 4 | 15 | 1k |
| 6p | 1 | 31.68 | 0.32 | 8 | 45 | 1k |
| 7p | 1 | 31.36 | 0.64 | 8 | 24 | 1k |
| 8p | 1 | 31.04 | 0.96 | 8 | 20 | 1k |
| 9p | 1 | 30.72 | 1.28 | 8 | 10 | 1k |
| 10p | 1 | 30.4 | 1.6 | 8 | 10 | 1k |
| 11p | 1 | 29.255 | 0.25 | 10.5 | 50 | 1k |
| 12p | 1 | 29.01 | 0.49 | 10.5 | 45 | 1k |
| 13p | 1 | 28.765 | 0.74 | 10.5 | 20 | 1k |
| 14p | 1 | 28.52 | 0.98 | 10.5 | 17.5 | 1k |
| 15p | 1 | 28.275 | 1.23 | 10.5 | 15 | 1k |
| 16p | 3 | 34.56 | 1.44 | 4 | 120 | 1k |
| 17p | 3 | 30.4 | 1.6 | 8 | 45 | 1k |

Example 1 b—Water Pick Up

A selection of the Samples made above were immersed in PBS and the increase of their weight (g) as a function of time is reported in Table 2.

TABLE 2

| sample | Dry weight before immersion (g) | Weight increase (g) | | | |
|---|---|---|---|---|---|
| | | 0 h | 22 h | 48 h | 72 h | 96 h |
| 1p | 4.197 | 0 | 0.201 | 0.256 | 0.282 | 0.320 |
| 3p | 6.313 | 0 | 0.121 | 0.159 | 0.199 | 0.214 |
| 5p | 5.863 | 0 | 0.091 | 0.148 | 0.175 | 0.208 |
| 6p | 5.646 | 0 | 0.273 | 0.39 | 0.465 | 0.521 |
| 9p | 7.69 | 0 | 0.245 | 0.355 | 0.441 | 0.514 |
| 10p | 5.16 | 0 | 0.185 | 0.261 | 0.339 | 0.389 |
| 11p | 5.064 | 0 | 0.351 | 0.498 | 0.601 | 0.689 |
| 13p | 4.553 | 0 | 0.432 | 0.453 | 0.552 | 0.658 |
| 15p | 2.764 | 0 | 0.281 | 0.44 | 0.536 | 0.638 |
| 11p | 5.589 | 0 | 0.351 | 0.498 | 0.601 | 0.689 |
| 16p | 3.108 | 0 | 0.106 | 0.132 | 0.157 | 0.185 |
| 17p | 3.137 | 0 | 0.276 | 0.519 | 0.493 | 0.514 |

One concludes that the inclusion of a water soluble resin in the compositions enables water to be adsorbed into the resulting cured elastomer as well as a having an SOT of less than 1 h. Surprisingly, although the resin is embedded within a hydrophobic matrix (silicone), the materials exhibit a substantial water pick up (table 2). Water uptake of the materials lead to the expansion on the testing specimens.

Example 1c—Stability

Two formulations (9p and 14p) were subsequently prepared on a on a larger scale (330 g) and stored in standard sealant cartridges. One cartridge was kept at room temperature (RT=22-23° C.) and another at 40° C.+/−2° C. for one week. The latter storage option is used to accelerate the aging of the material. Two mm thick sheets have been casted from the fresh and aged sealant and allowed to cure at RT (22-23° C.) at 50% relative humidity for 7 days. Test dumbbells have been cut and the mechanical properties of these specimens tested following ASTM D 412-06. It will be appreciated from the results in Table 3 that the mechanical properties upon ageing at 40° C. remain comparable within 25% to the initial values. The SOT does not exceed 70 min.

TABLE 3

| | | Formulation 9p- fresh | Formulation 14p- fresh | Formulation 9p 1 wk @ 40 C. | Formulation 14p -1 wk @40 C. |
|---|---|---|---|---|---|
| | SOT (min) | 31 | 15 | 65 | 43 |
| | CID 1 day (mm) | 3.2 | 3.6 | | |
| Dumbbells 7 Days cure | Tensile strength (MPa) | 0.61 | 1.03 | 0.51 | 0.77 |
| | Elongation at Break* (%) | 113 | 117 | 141 | 123 |

*also called ultimate elongation in ASTM 412 D - 06

Example 1d—Large Scale Preparation

In a 5 L compounder 4000 g of the following sealant was prepared:

| Ingredient | Wt % |
|---|---|
| trimethoxy silyl terminated siloxane polymer with viscosity of about 63000 mPa · s at 25° C. | 33.6 |
| 1,6-bis(trimethoxy silyl)hexane | 1.6 |
| Polyox WSR 205 | 30.4 |
| Trimethyl siloxy-terminated polydimethyl siloxane with zero shear viscosity of 3000 Pa · s | 33.6 |
| Tetra-n-butyltitanate (TNBT) | 0.8 |

The material was immediately packed in standard sealant cartridges (ca. 330 g per cartridge). 24 h after the packaging some of the cartridges were stored in an oven at 40 C, the rest were kept in room temperature (22-23° C.). 24 h after packaging the sealant was successfully extruded using a manual cartridge gun. After one week of storage in an oven at 40° C. the sealant was successfully extruded using a manual cartridge gun and no difference in appearance and extrudability was observed in comparison with the fresh sealant.

Example 2 Compositions Using Component B (ii) Anionic Surfactants

Example 2a—Composition

The methodology described in example 1a is used, but the water pick up component was an anionic surfactant B (ii). Following materials were used: Bioterge® AS90 (commercial material from Stepan) sodium alpha-olefine sulphonate
Hostapur® SAS 93 G (commercial material from Clariant) Secondary alkane sulphonate, sodium salt.
Nacconol® 90 G (commercial material from Stepan) Sodium (C10-16) benzenesulphonate
Dispolil® SLS 128 (commercial materials from Cognis) Sodium lauryl sulphates (C12-C18)
Table 4 shows the formulation, the type of cure and SOT. Table 5 shows the water pick up of selected formulations; stability data is shown in Table 6.

TABLE 4

| formulation | MB used | MB, Amount (g) | Catalyst (g) | Anionic amount used | Anionic Surfactant surfactant (g) | SOT (min) | Type Of cure |
|---|---|---|---|---|---|---|---|
| 1-as | 1 | 23.76 | 0.24 | Bioterge AS 90 | 6 | 50 | 2K |

TABLE 4-continued

| formulation | MB used | MB, Amount (g) | Catalyst (g) | Anionic amount used | Anionic Surfactant surfactant (g) | SOT (min) | Type Of cure |
|---|---|---|---|---|---|---|---|
| 2-as | 1 | 23.52 | 0.48 | Bioterge AS 90 | 6 | 30 | 2K |
| 3-as | 1 | 23.28 | 0.72 | Bioterge AS 90 | 6 | 15 | 1K |
| 4-as | 1 | 23.04 | 0.96 | Bioterge AS 90 | 6 | 13 | 1K |
| 5-as | 1 | 22.8 | 1.2 | Bioterge AS 90 | 6 | 10 | 1K |
| 6-as | 2 | 27.4 | 0.6 | Bioterge AS 90 | 2.04 | 25-30 | 1k |
| 7-as | 3 | 27.42 | 0.6 | Bioterge AS 90 | 2.04 | | 1K |
| 8-as | 1 | 27.16 | 0.84 | Hostapur SAS 93G | 7 | >240 | 1k |
| 9-as | 1 | 26.88 | 1.12 | Hostapur SAS 93G | 7 | 20 | 1k |
| 10-as | 1 | 26.6 | 1.4 | Hostapur SAS 93G | 7 | 18 | 1k |
| 11-as | 1 | 26.19 | 0.81 | Hostapur SAS 93G | 3 | | 1k |
| 12-as | 1 | 25.65 | 1.35 | Hostapur SAS 3G | 3 | | 1k |
| 13-as | 1 | 26.88 | 1.12 | Nocconol 90G | 7 | 13-16 | 2k |
| 14-as | 1 | 26.88 | 1.12 | Disponil SLS 128 | 7 | 15 | 1k |

Example 2b—Water Pick-Up

The methodology described in example 1b was repeated to evaluate the water pick up of some formulations containing anionic surfactants

TABLE 5

Water pick-up in grams

| Formulation | Dry weight before immersion, g | Weight increase upon immersion, (g) | | |
|---|---|---|---|---|
| | | 0 h | 22-24 h | 48 h | 120 h |
| 3-as | 7.162 | 0 | 0.476 | 0.780 | 1.205 |
| 4-as | 5.788 | 0 | 0.368 | 0.571 | 0.941 |
| 5-as | 5.035 | 0 | 0.337 | 0.508 | 0.887 |
| 6-as | 5.047 | 0 | 0.179 | 0.274 | 0.425 |
| 7-as | 3.961 | 0 | 0.087 | 0.138 | 0.238 |
| 8- as | 4.909 | 0 | 0.074 | 0.091 | |
| 10-as | 4.148 | 0 | 0.118 | 0.165 | |
| 11-as | 5.308 | 0 | 0.098 | 0.133 | |
| 12-as | 5.259 | 0 | 0.076 | 0.108 | |

Example 2c Stability

Following the methodology described in example 1c sample 10 as have been studied.

TABLE 6

| | Formulation fresh-10as | Formulation 10as 1 wk @ 40 C. |
|---|---|---|
| SOT (min) | 41 | 63 |
| CID 1 day (mm) | 2.0 | |
| Dumbbells 7 Days cure | Tensile strength (MPa) | 0.23 | 0.28 |
| | Elongation at Break* (%) | 72 | 175 |

*also called ultimate elongation in ASTM 412 D - 06

Example 3 Composition Containing Component B (iii) a Commercial Polymer with Pendant Sulphonic Groups and PVA Material used was Polyvinyl Alcohol (commercial name Mowiol® 5-88) commercially available form KURARAY. Table 7 show the composition of the sealants made with PVA.

TABLE 7A

| Number | MB used | MB, amount (g) | MB, amount (g) | PVA (g) | SOT (min) | Type of cure |
|---|---|---|---|---|---|---|
| 1i | 1 | 30.24 | 1.26 | 3.5 | 60+ | 2k |
| 2i | 1 | 29.925 | 1.575 | 3.5 | 60+ | 2k |
| 3i | 1 | 26.88 | 1.12 | 7 | 60+ | 2k |
| 4i | 1 | 26.6 | 1.4 | 7 | 60+ | 2k |

Table 7b water pick up material was sodium polystyrene sulphonate with MW of 75000 D, commercially available form Alfa Aesar

TABLE 7B

| Number | MB used | MB, amount (g) | MB, amount (g) | NaPSS | SOT (min) | Type of cure |
|---|---|---|---|---|---|---|
| 5i | 1 | 23.52 | 0.98 | 10.5 | 50 | 2k |
| 6i | 1 | 23.275 | 1.23 | 10.5 | 40-45 | 2k |
| 7i | 2 | 23.52 | 0.98 | 10.5 | ~120 | 2k |
| 8i | 2 | 26.6 | 1.23 | 10.5 | ~120 | 2k |
| 9i | 1 | 30.87 | 0.63 | 3.5 | 90 | 2k |
| 10i | 1 | 30.555 | 0.945 | 3.5 | 70 | 2k |
| 11i | 1 | 30.24 | 1.26 | 3.5 | 70 | 2k |
| 12i | 1 | 29.925 | 1.575 | 3.5 | 30 | 2k |
| 13i | 1 | 27.16 | 0.84 | 7.0 | 80-90 | 2k |
| 14i | 1 | 26.88 | 1.12 | 7.0 | 40-50 | 2k |
| 15i | 1 | 26.6 | 1.4 | 7.0 | 40 | 2k |
| 16i | 2 | 26.74 | 1.26 | 7.0 | >120 | 2k |
| 17i | 2 | 26.42 | 1.575 | 7.0 | >120 | 2k |

The invention claimed is:
1. A silicone room temperature curable sealant/adhesive composition comprising:
(A) at least 50% by weight of one or more organopolysiloxanes selected from:
(i) $(R''O)_{3-a}(R)_a Si—Z—(Si(R)_2—O)_x—Si(R)_2—Z—Si(OR'')_{3-a}(R)_a$ where each R is free of aliphatic unsaturation and is independently selected from the group consisting of monovalent hydrocarbon, monovalent halohydrocarbon, and monovalent cyanoalkyl radicals having from 1 to 18 carbon atoms, each R" is independently a monovalent hydrocarbon group having 1 to 6 carbon atoms, Z is a divalent hydrocarbon radical or combination of divalent hydrocarbon radicals and siloxane radicals, a is 0 or 1, and x is of a value such that component (A)(i) has a viscosity of from 0.5 to 3000 Pas at 25° C.;
(ii) alpha, omega-diorganopolysiloxane of the formula

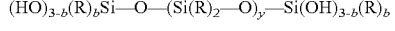

$(HO)_{3-b}(R)_b Si—O—(Si(R)_2—O)_y—Si(OH)_{3-b}(R)_b$ where each R is free of aliphatic unsaturation and is independently selected from the group consisting of monovalent hydrocarbon, monovalent halohydrocarbon, and monovalent cyanoalkyl radicals having from 1 to 18 carbon atoms, b is 0, 1 or 2, and y is of a value such that component (A)(ii) has a viscosity of from 0.5 to 3000 Pas at 25° C. and a number average molecular weight ($M_n$) of from 1000 to 1000000; or (iii) mixtures of the above;

(B) 5 to 35% by weight of a hydrophilic material comprising (B)(iii) polymers containing ionisable groups;

(C) 0.5 to 7.5% by weight of a cross-linker selected from a silane or siloxane cross linker containing at least two alkoxy or alkenyloxy groups, or silyl functional molecules having at least two silyl groups, each silyl group containing at least one alkoxy or alkenyloxy group;

(D) 0.5 to 5% by weight titanate or zirconate catalyst; and (E) optionally, one or more ingredients selected from fillers, co-catalysts, rheological modifiers, plasticisers, adhesion promoters, compatibilizers, pigments, heat stabilizers, flame retardants, UV stabilizers, chain extenders, electrically and/or heat conductive fillers, and/or fungicides/biocides;

wherein the total % by weight of components (A)+(B)+(C)+(D)+(E) is 100%; and wherein the hydrophilic material is selected from homopolymers and copolymers comprising vinylsulphonic, styrenesulphonic, naphthalenesulphonic or acrylamidoalkylsulphonic units and their salts and also copolymers thereof with an unsaturated comonomer.

2. The silicone room temperature curable sealant/adhesive composition in accordance with claim 1, wherein component (B) is component (B)(iii).

3. The silicone room temperature curable sealant/adhesive composition in accordance with claim 1, stored before use in one or two parts.

4. The silicone room temperature curable sealant/adhesive composition in accordance with claim 1, which is a one-component composition which, when stored at a temperature above 30° C., prior to cure retains at least 50% of its mechanical strength upon cure.

5. A silicone elastomer resulting from curing the silicone room temperature curable sealant/adhesive composition in accordance with claim 1.

6. The silicone elastomer of claim 5, having a water pick up of at least 0.01 gram of water per gram of silicone elastomer, when the silicone elastomer is immersed in water or phosphate buffer saline for 24 h.

7. A sealant comprising the silicone elastomer in accordance with claim 5.

8. A method of controlling and/or restraining aqueous leaks, said method comprising disposing a silicone elastomer where joint expansion is desired, wherein the silicone elastomer is the silicone elastomer in accordance with claim 6.

9. A patch comprising the silicone elastomer in accordance with claim 5.

10. A method of filling a space defined between two substrates so as to form an arrangement, the method comprising:

a) providing the silicone room temperature curable sealant/adhesive composition in accordance with claim 1;

b1) applying the composition to a first substrate, and bringing a second substrate in contact with the composition that has been applied to the first substrate; or b2) filling a space defined by a first substrate and a second substrate with the composition; and c) curing the composition, thereby forming the arrangement.

11. The silicone room temperature curable sealant/adhesive composition in accordance with claim 1, wherein component (E) is present.

12. A medical device comprising the silicone elastomer in accordance with claim 5.

13. A diaper comprising the silicone elastomer in accordance with claim 5.

14. The silicone room temperature curable sealant/adhesive composition in accordance with claim 1, wherein component (B) comprises a mixture of component (B)(iii) and (B)(i) hydrophilic and/or water soluble resins based on polyethylene oxide and/or polypropylene oxide.

15. The silicone room temperature curable sealant/adhesive composition in accordance with claim 14, wherein component (B)(i) comprises polyoxyalkylene polymers comprising recurring oxyalkylene units illustrated by the average formula $(-C_nH_{2n}-O-)_y$, wherein n is an integer from two to four and y is an integer of at least four.

16. The silicone room temperature curable sealant/adhesive composition in accordance with claim 15, wherein the number average molecular weight of each polyoxyalkylene polymer is greater than 50000.

17. The silicone room temperature curable sealant/adhesive composition in accordance with claim 1, wherein component (B) comprises a mixture of component (B)(iii) and (B)(ii) one or more anionic surfactants.

18. The silicone room temperature curable sealant/adhesive composition in accordance with claim 17, wherein the one or more anionic surfactants (B)(ii) are selected from sodium/potassium sulphonates, alkenyl sulphonates, alkyl sulphates, alkyl-benzene sulphonates, potassium alkyl phosphates, alkyl succinates, alkyl sulphosuccinates and N-alkyl sarcosinates and sodium, magnesium, ammonium, and the mono-, di- and triethanolamine salts of alkyl and aralkyl sulphates as well as the salts of alkaryl sulphonates and/or mixtures thereof.

19. The silicone room temperature curable sealant/adhesive composition in accordance with claim 17, wherein component (B) comprises a mixture of components (B)(iii) and (B)(ii) and (B)(i) hydrophilic and/or water soluble resins based on polyethylene oxide and/or polypropylene oxide.

20. The silicone room temperature curable sealant/adhesive composition in accordance with claim 19, wherein:

component (B)(i) comprises polyoxyalkylene polymers comprising recurring oxyalkylene units illustrated by the average formula $(-C_nH_{2n}-O-)_y$, wherein n is an integer from two to four and y is an integer of at least four; and the one or more anionic surfactants (B)(ii) are selected from sodium/potassium sulphonates, alkenyl sulphonates, alkyl sulphates, alkyl-benzene sulphonates, potassium alkyl phosphates, alkyl succinates, alkyl sulphosuccinates and N-alkyl sarcosinates and sodium, magnesium, ammonium, and the mono-, di- and triethanolamine salts of alkyl and aralkyl sulphates as well as the salts of alkaryl sulphonates and/or mixtures thereof.

* * * * *